United States Patent
Yellin et al.

(10) Patent No.: US 11,670,423 B2
(45) Date of Patent: Jun. 6, 2023

(54) METHOD AND SYSTEM FOR EARLY DETECTION OF NEURODEGENERATION USING PROGRESSIVE TRACKING OF EYE-MARKERS

(71) Applicant: BIOEYE LTD., Hofit (IL)

(72) Inventors: Dov Yellin, Kfar Saba (IL); Eran Ferri, Hofit (IL)

(73) Assignee: BIOEYE LTD., Hofit (IL)

( * ) Notice: Subject to any disclaimer, the term of this patent is extended or adjusted under 35 U.S.C. 154(b) by 428 days.

(21) Appl. No.: 16/762,433

(22) PCT Filed: Nov. 11, 2018

(86) PCT No.: PCT/IL2018/051212
§ 371 (c)(1),
(2) Date: May 7, 2020

(87) PCT Pub. No.: WO2019/092722
PCT Pub. Date: May 16, 2019

(65) Prior Publication Data
US 2021/0186318 A1    Jun. 24, 2021

(30) Foreign Application Priority Data
Nov. 12, 2017 (IL) .......................... 255607

(51) Int. Cl.
*G16H 50/30* (2018.01)
*A61B 3/00* (2006.01)
(Continued)

(52) U.S. Cl.
CPC ........... *G16H 50/30* (2018.01); *A61B 3/0025* (2013.01); *A61B 5/7267* (2013.01);
(Continued)

(58) Field of Classification Search
CPC .. G06K 9/6256; A61B 5/7267; A61B 3/0025; A61B 2576/02; A61B 5/4878; G16H 50/30; G06N 20/20
(Continued)

(56) References Cited

U.S. PATENT DOCUMENTS 9,198,571 B2 * 12/2015 Kiderman ............... A61B 3/005
9,247,870 B2 *  2/2016 Kiderman ............... A61B 3/113
(Continued)

FOREIGN PATENT DOCUMENTS

CN    106295163 A      1/2017
CN    106419831 A  *  2/2017
(Continued)

OTHER PUBLICATIONS

Mariakakis et al., PupilScreen: Using Smartphone to Assess Traumatic Brain injury,. Sep. 2017, Proceeding of the ACM on Interactive, Mobile, Wearable and Ubiquitous Technologies, vol. 1, No. 3., pp. 1-28. (Year: 2017).*
(Continued)

*Primary Examiner* — Ishrat I Sherali
(74) *Attorney, Agent, or Firm* — Roach, Brown, McCarthy & Gruber, P.C.; Kevin D. McCarthy

(57) ABSTRACT

A method and system for the early detection of neurodegeneration are described. The method comprises the steps of: a) extracting samples of a plurality of eye-markers of a user from a video stream captured by a visible light camera; b) loading said samples of said plurality of eye-markers to a big data repository, analyzing and consolidating them into one biomarker for detecting multiple disorders by means of training a machine learning model; and c) determining the risk of said user to develop a neurodegenerative disease using said trained machine learning model as part of an early detection screening or diagnosis process.

16 Claims, 6 Drawing Sheets

(51) Int. Cl.
　　*A61B 5/00*　　　(2006.01)
　　*G06N 20/20*　　(2019.01)
　　*G06F 18/214*　　(2023.01)

(52) U.S. Cl.
　　CPC ........... *G06F 18/214* (2023.01); *G06N 20/20* (2019.01); *A61B 5/4878* (2013.01); *A61B 2576/02* (2013.01)

(58) Field of Classification Search
　　USPC .......................................... 382/128; 351/206
　　See application file for complete search history.

(56) References Cited

U.S. PATENT DOCUMENTS

| | | | |
|---|---|---|---|
| 9,814,430 | B1 | 11/2017 | Berme et al. |
| 10,537,276 | B2 * | 1/2020 | Macknik .............. A61B 5/4842 |
| 10,835,167 | B2 * | 11/2020 | Voss ...................... G06V 10/255 |
| 2014/0114889 | A1 | 4/2014 | Dagum |
| 2016/0142894 | A1 * | 5/2016 | Papakonstantinou .. G16H 40/67 455/404.1 |
| 2017/0311799 | A1 | 11/2017 | Holt et al. |
| 2017/0357879 | A1 | 12/2017 | Odaibo et al. |
| 2018/0121608 | A1 | 5/2018 | Gross et al. |
| 2018/0125356 | A1 | 5/2018 | Yamada |
| 2018/0125404 | A1 * | 5/2018 | Bott ....................... G06V 20/59 |
| 2018/0125405 | A1 | 5/2018 | Yamada |
| 2018/0125406 | A1 | 5/2018 | Yamada |
| 2019/0343382 | A1 * | 11/2019 | Rubner ................. G06F 3/0481 |
| 2020/0121237 | A1 * | 4/2020 | Yellin .................... A61B 5/163 |
| 2022/0280098 | A1 * | 9/2022 | Hao ...................... A61B 5/0004 |

FOREIGN PATENT DOCUMENTS

| | | |
|---|---|---|
| CN | 106419831 A | 2/2017 |
| KR | 101556601 B1 | 10/2015 |
| RU | 2017105271 A | 8/2018 |
| WO | 2018/046957 A2 | 3/2018 |
| WO | 2018/142388 A | 8/2018 |

OTHER PUBLICATIONS

Sara, 2009, The locus coeruleus and noradrenergic modulation of cognition. Nat Rev Neurosci 10, 211-223 (13 pages).
Peshori et al. (2001) Aging of the trigeminal blink system. Exp Brain Res 136, 351-363 (14 pages).
Anderson and MacAskill 2013 Eye movements in patients with neuradegenerative disorders. Nat Rev Neurology 9, 74-85 (12 pages).
Siuly et al., "Medical Big Data: Neurological Diseases Diagnosis Through Medical Data Analysis"; Data Sci. Eng. (2016) 1(2):54-64 (11 pages).
International Search Report for PCT/IL2018/051212, dated Feb. 7, 2019; 4 pages.
Written Opinion of the International Searching Authority for PCT/IL2018/051212, dated Feb. 7, 2019; 6 pages.

* cited by examiner

METHOD AND SYSTEM FOR EARLY DETECTION OF NEURODEGENERATION USING PROGRESSIVE TRACKING OF EYE-MARKERS

FIELD OF THE INVENTION

The invention relates to the field of monitoring trends in human cognitive health through the analysis of data extracted from users' eyes, by means of image processing and machine learning. More specifically, the invention relates to an application and compound method for ongoing monitoring and screening of eye markers of healthy individuals for determining their risk of developing neurodegenerative diseases.

BACKGROUND OF INVENTION

Neurodegeneration is the progressive structural and functional loss of brain tissue, including death of neurons. It is a condition that leads to a spectrum of cognitive decline related diseases, some of which bear grave outcome, such as in the case of Alzheimer's disease. The spectrum of neurodegenerative diseases includes a number of different indispositions, such as Parkinson's disease (PD), amyotrophic lateral sclerosis (ALS), Huntington's disease (HD), Alzheimer's disease (AD) and various other types of dementia. During early stage of neurodegeneration, lighter forms of decline may manifest themselves, as in the form of 'Mild Cognitive Impairment' (MCI), a condition which in some individuals may further progress into the full expression of AD. To date, the entire spectrum of neurodegenerative diseases is all incurable, resulting in advancing cognitive functional decline. A commonality of the entire spectrum is that, in all, neurons gradually and selectively lose function as the disease progresses with age.

Following decades of research, there is a growing present consensus within the scientific and medical communities arguing that pre-clinical early detection of cognitive decline is the future key to prevention, recovery and resolution of neurodegeneration. Hence a search for accurate biomarkers for the early detection of cognitive decline, even before clinical symptoms are evident, has become a top priority. Biomarkers are useful in determining the risk, but are also invaluable in establishing early diagnosis and an intervention plan. As DNA signature based biomarkers for neurodegeneration are presently nonexistent, the leading methods of early clinical diagnosis are positron emission tomography (PET) scan (both amyloid and tau versions), and cerebrospinal fluid (CSF) test. However, both are expensive and intrusive, rendering them impractical for wide population screening. Consequently, the quest for widely accessible yet accurate enough cognitive decline physiological biomarkers remains a challenge.

It is therefore an object of the present invention to provide a method for early detection of cognitive decline using ongoing monitoring of trends in various eye-marker measures. Going into finer detail, it is an object of the present invention to provide a method consisting of a compound system connecting together an application for seamless eye-marker data collection based on specialized image processing and machine learning algorithms, and unique feature generation process targeting the early detection of neurodegeneration presence and dynamics.

Further objects and advantages of the invention will become evident as the description proceeds.

SUMMARY OF THE INVENTION

In one aspect the invention relates to a method for the early detection of neurodegeneration, comprising the steps of: extracting samples of a plurality of eye-markers of a user from a video stream captured by a visible light camera; loading said samples of said plurality of eye-markers to a big data repository, analyzing and consolidating them into one biomarker for detecting multiple disorders by means of training a machine learning model; and determining the risk of said user to develop neurodegenerative disease using said trained model as part of an early detection screening or diagnosis process.

In an embodiment of the invention, the method further comprises analyzing said samples of plurality of eye-markers, transforming some of said samples into derived features, to generate multiple features optimized for use within a machine learning model, using computational methods for feature extractions.

In an embodiment of the invention, the computational methods are selected from one or more of: Fourier transform, wavelet analysis differentiating certain frequency bands, criticality metrics based on Lyapunov exponents and fractal dimension analysis.

In an embodiment of the invention, one or more eye markers are extracted at a time.

In an embodiment of the invention, the eye-markers extracted are selected from one or more of the following: pupil size, eye movements, blinks and gaze.

In an embodiment of the invention, the eye-markers are collected separately from each eye of the user as separate features of the machine learning model.

In an embodiment of the invention, the derived features are based on the feature of each eye separately or on a function of the features of the two eyes.

In an embodiment of the invention, the step of extracting samples is performed using one of the following: webcam, smartphone front or back camera, a camera of a Virtual Reality device, a camera of an Augmented Reality device, a camera of a wearable device or a scientific-grade IR eye-tracker.

In an embodiment of the invention, the analysis of eye-markers, machine learning and consolidation to a biomarker take place over the cloud or on a local computer.

In an embodiment of the invention, an additional machine learning features, besides the eye-markers, are collected from other device sensors during the eye tracking sessions.

In an embodiment of the invention, the method further comprises a user registration step, wherein a face recognition algorithm is used during user registration to differentiate the identity of said user from other occasional users of the device.

In another aspect the invention relates to a system for the early detection of neurodegeneration, comprising:
a. a camera of a mobile device or of Virtual Reality device or of an Augmented reality device for capturing video of one or both of the eyes of a user and extracting a plurality of eye marker samples;
b. a big data repository for aggregating said plurality of eye-marker samples over time;
c. a machine learning module for analyzing said captured plurality of eye marker samples for consolidating said plurality of eye markers into a trained machine learning model reflecting a single biomarker; thereby, providing a prediction of an early stage diagnosis determining the risk of said user to develop neurodegenerative diseases.

All the above and other characteristics and advantages of the invention will become well understood through the following illustrative and non-limitative description of embodiments thereof, with reference to the appended drawings.

DETAILED DESCRIPTION OF THE EMBODIMENTS OF THE PRESENT INVENTION

The present invention relates to a method consolidating different measures from the eyes (aka eye-markers) into single combined biomarkers for the early detection of cognitive decline.

In an embodiment of the invention, the method uses a mobile eye-tracking application, implementing an ongoing, day-by-day, monitoring of eyes of users to capture daily video samples of the user's eyes, and transform these samples into eye-markers.

In one embodiment the monitoring of the eyes of users to capture daily video samples of the user's eyes is done while the user engages normal activities of the mobile device for example: reading emails, reading text messages etc.

In another embodiment the monitoring of the eyes of users to capture daily video samples of the user's eyes is done while the user engages in one or more activities predefined by the application and system of the invention.

The method of the invention loads the plurality of eye-markers onto a remote server on the cloud where they are analyzed, transforming some of their time-series as needed into derived features, to generate multiple features optimized for use within a machine learning model. A variety of computational methods for time-series based features are used in this transformation from raw features to derived ones, including but not limited to: Fourier transform and wavelet analysis differentiating certain frequency bands, criticality metrics based on Lyapunov exponents and fractal dimension analysis. Further use of sliding-window analysis enables analysis of the variance of abovementioned raw and derived features over time.

Figure 1:
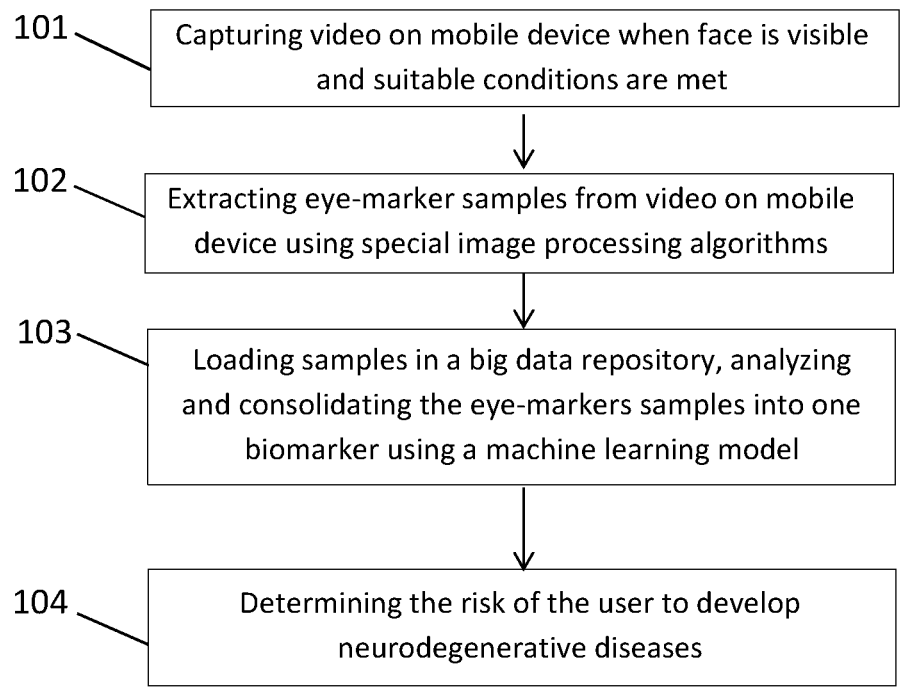
FIG. 1: schematically shows the method of the invention according to an embodiment of the invention.

FIG. 1 schematically describes the method of the present invention. In an embodiment of the invention, the method comprises the following steps: first in step 101 a video is captured by a camera of a smartphone (front or back camera) or of a computer (a webcam) and, in step 102, data samples (as time-series) of eye-markers are extracted from the video in real-time without need of saving the video to the device's hard-disk, in addition the camera used may be a visible light camera or an Infra-red (IR) camera. Then in the next step 103, the eye-markers samples are uploaded and accumulated into a remote big-data repository over the cloud. The eye markers samples are analyzed and consolidated along with their trend through a machine learning model into one biomarker, which detects multiple disorders. More specifically, in the big data repository, aggregated over time per each individual and over the large population, the eye markers serve as features and as basis for generation of additional computed features, for use in training a machine learning model and then within a prediction process, separating between healthy and unhealthy individuals (i.e. those showing early signs of neurodegeneration). The additional use of sophisticated big data analytics for cleansing and improving raw features, culminates into higher quality synthetized features for even more accurate diagnostic competency. Eventually in step 104, the risk of the user to develop a neurodegenerative disease is determined (and in many cases a neurodegenerative disease of a specific type can be determined), as part of an early detection screening or diagnosis process based on usage of the trained machine learning model for predicting an ongoing measure of said biomarker results.

In general, eye markers are divided to four main categories, each of which is a manifestation of processes controlled and operated in a different area in the brain:
1. Pupil size—affected by activity of the Locus Coeruleus (LC) nucleus in the brain stem—the hub of noradrenaline (NE) neurotransmitter generation in the brain;
2. Spontaneous blinking—related to the dopaminergic system residing primarily in the striatum;
3. Eye movements—which relates to fixations and saccades and are tightly connected to cortical and thalamic activity; and
4. Gaze—which indicates what and where the person is looking at and is related to activity in the frontal eye field (FEF) and additional cortical and thalamic areas.

Prior art documents disclose the use of a single eye marker at a time as a part of research on a specific area of the brain, wherein this specific area of the brain is associated to a specific cognitive decline disease for example: Sara, 2009, The locus coeruleus and noradrenergic modulation of cognition. Nat Rev Neurosci 10, 211-223 relates to pupil size, Peshori et al. (2001) Aging of the trigeminal blink system. Exp Brain Res 136, 351-363 relates to spontaneous blinking and Anderson and MacAskill 2013 Eye movements in patients with neurodegenerative disorders. Nat Rev Neurology 9, 74-85 relates to eye movements.

However, the present invention unifies the contribution of different eye-markers by processing and consolidating them, by means of training a machine learning model, into a single more powerful biomarker. Specifically, this consolidation process in achieved via the following general multiclass (for multiple types of disorders) supervised machine learning schema:

$$Y_i^j = H_\theta(x_i^k) + \varepsilon_i$$

where $H_\theta$ is a function denoting the actual prediction model (or in simpler terms, the biomarker), which the system is trained to learn. The symbol $Y_i^j$ denotes the ground truth per sample, as a vector of the multiclass labels for j classes (i.e. the number neurodegenerative diseases the system is trained over), where i is the sample index (i.e. a running enumerator of subjects' eye-markers periodic sample). The symbol $\theta$ denotes a squashing function used by the machine learning model in use (which may be of linear or non-linear nature). The symbol $x_i^k$ denotes the features matrix, consisting of k raw and derived eye-marker features, and $\varepsilon_i$ is the error per sample which is minimized during the training process.

In one embodiment of the present invention, a supervised feedforward deep-learning model with few hidden layers of relu neurons and a softmax output layer is used. The raw and derived features include cross-day calculation of average, variance and trend metrics based on the different eye-markers values.

In another embodiment of the present invention, the Long Short Term Memory (LSTM) deep learning method is used as the selected algorithm of the said machine learning approach. In this embodiment, features are derived and based on the local statistics of daily eye-markers, allowing the algorithm to learn the gradual shift associated with the difference in these statistics between healthy and abnormal (neurodegenerative related) markers. Clearly, other equivalent machine learning methods may be applied as well.

Thus, using the abovementioned machine learning model schemes, an accurate means for early detection of various types of neurodegeneration is achieved. To summarize, the method of the present invention relates to a set of indicators consolidated into a single biomarker for the detection of multiple disorders. The method relies on the capture of different eye markers and their collective analysis within a big data repository, using machine learning based modeling.

In an embodiment of the invention the eye-markers are collected from both eyes separately, whereas derived features may be based on the base features of each eye separately or on some function of the features of the two eyes.

In an embodiment of the invention, an additional machine learning features, besides the eye-markers, are collected from other device sensors during the eye tracking sessions.

Figure 2:
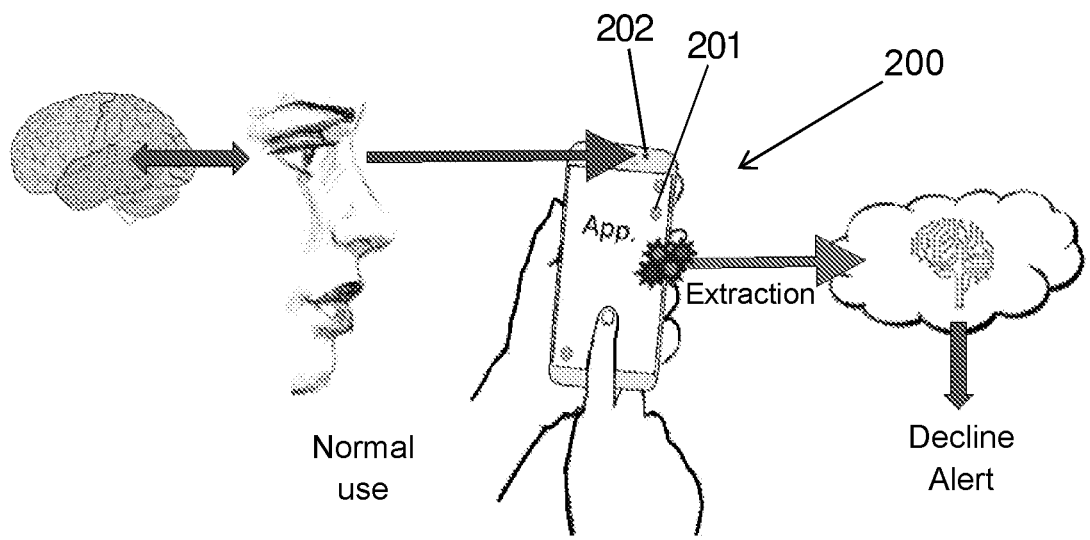
FIG. 2 schematically shows an illustration of a device usage through extraction of eye-marker samples during regular operation of the user's smartphone according to an embodiment of the invention.

FIG. 2 schematically shows the system of the invention according to an embodiment of the invention. In one embodiment of the invention, system 200 consists of a smartphone application 201 or a laptop webcam, that uses a standard camera's visible light video 202 for mobile eye-tracking and capturing of meaningful eye-markers as disclosed in WO 2018/142388. Clearly, an alternative option of using a scientific grade IR eye-tracker may remain valid as well. The extraction of eye-marker samples is done during regular operation of the smartphone of the users. Eye-tracking via smartphone front camera will take place only when usage profile is suitable, in aim of capturing only few minutes of continuous samples per day. Extracted eye-marker samples are later uploaded to a big-data repository.

After its installation and registration, the application works in interactive mode engaging the user in a preselected activity (such as reading mail or viewing news clips), or at background without any interference with the user's regular usage of the device (smartphone or webcam). During an initial registration process the application potentially applies a face recognition algorithm to detect and learn the identity of the designated user. The outcome face recognition model of this learning process, based on the personalized features of the user's face serves for determining when the designated user is at view in order to initiate daily data collection. In an embodiment of the invention it also serves to improve the reliability and accuracy of imminent eye detection and measurement algorithms, by personalizing internal algorithm parameters based on specific properties of the designated user's face, later to be used as part of the specialized image processing for accurate extraction of eye-markers.

In an embodiment of the invention, the application monitors the device usage in aim of identifying well-suited opportunities for collecting eye data. When a face is in view of the camera, lighting conditions are fair, load on the device processor is within a suitable range and further technical criteria are met, such as sufficient power reserve and limited tilt acceleration levels, the device seamlessly captures a few minutes of video from both eyes. Optionally, data collection is limited to incidents of automatic identification of the designated user (by real-time identity recognition). This is to overcome cases in which there may be more than one person who occasionally uses the device. During a single typical day of usage, roughly 2-10 minutes of video provide an optimal amount of data for proper long-term function of the method. However, lack of daily usage does not prevent proper functioning of the method as long as data accumulation consists over the longer period (of few weeks or months). That being said, whenever opportunities to collect additional high quality data are applicable, they may be seized.

Figure 3:
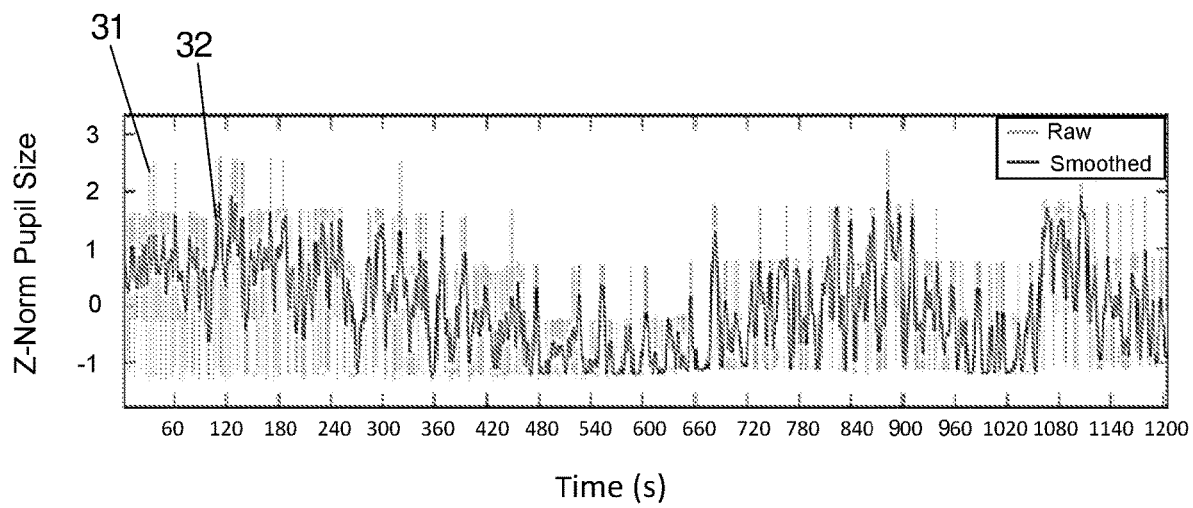
FIG. 3 schematically shows a few-minutes sample of pupil size time-course during spontaneous behavior according to an embodiment of the invention.

In an embodiment of the invention, eye-markers are extracted from the device, i.e. the video stream is processed when the device usage conditions facilitate, transforming the video into vectors of numbers reflecting time-course data of relevant eye-markers. The video stream duration of each data sample has duration of ideally two minutes or longer. But sliding-window analysis facilitates feature extraction from any interval in this period. FIG. 3 illustrates one of these markers—a sample pupil size time-course. Signal 31 represent a few-minutes sample of pupil size time-course during spontaneous behavior. Signal 31 is presented, as obtained by the device. Signal 32 is a result after applying standard corrections, i.e. the raw signal after being preprocessed and smoothed, as to derive a typical physiological pupil fluctuation pattern.

The different eye-marker vectors obtained from the camera are then uploaded to a remote server (over the cloud) where they are further cleansed and processed to obtain derived features. Special processing methods applied to each of the markers include cleansing artifacts, filtering out noisy frequencies, interpolation of momentary signal loss and smoothing of the outcome. Derived features are based on standard and proprietary signal processing methods as well as on recent scientific findings pertaining to the different eye-markers in use. The features are then stored in the long-term big-data repository of eye-markers, where they serve as input for features supporting models generated by applying machine learning training algorithms.

In an embodiment of the invention, the diagnosis of a user's cognitive state, based on said models for detection of neurodegeneration, take place over the cloud assuming accumulation of daily data that was uploaded previously. In another embodiment, a trained model may reside on the end device, allowing for predictions to be computed locally.

Figure 4A:
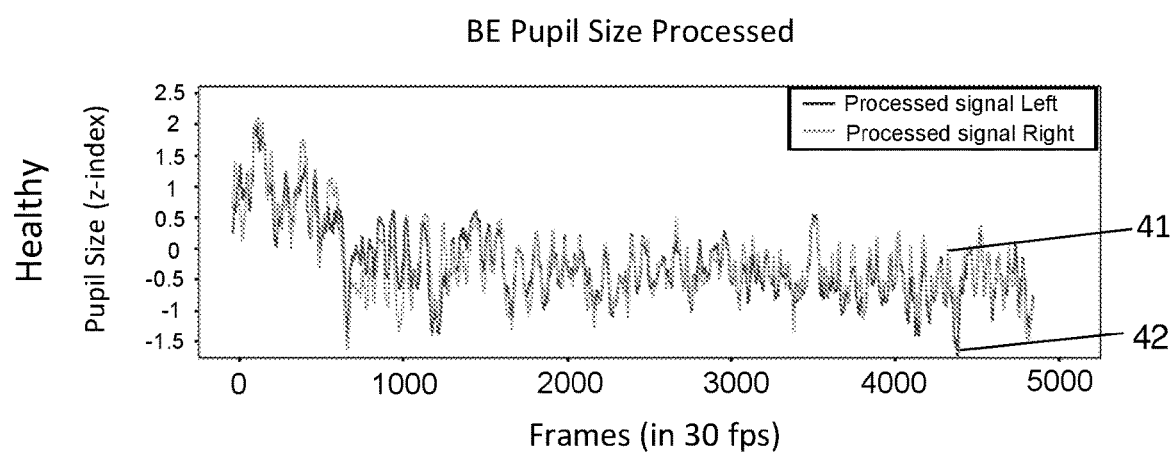
FIGS. 4a-4c schematically presents and compares pupil size time-course results from normal, Parkinson's and MCI users of the technology according to an embodiment of the invention.
Figure 4B:
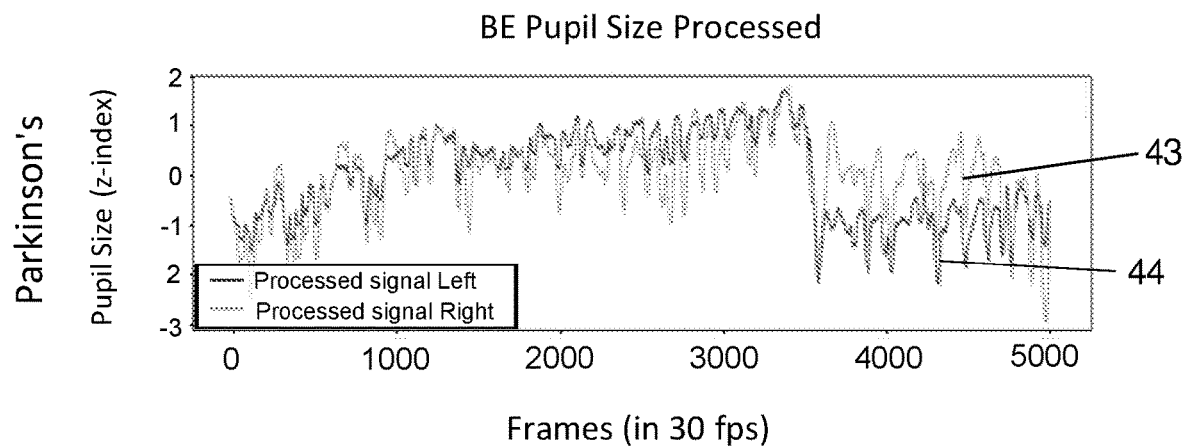
Figure 4C:
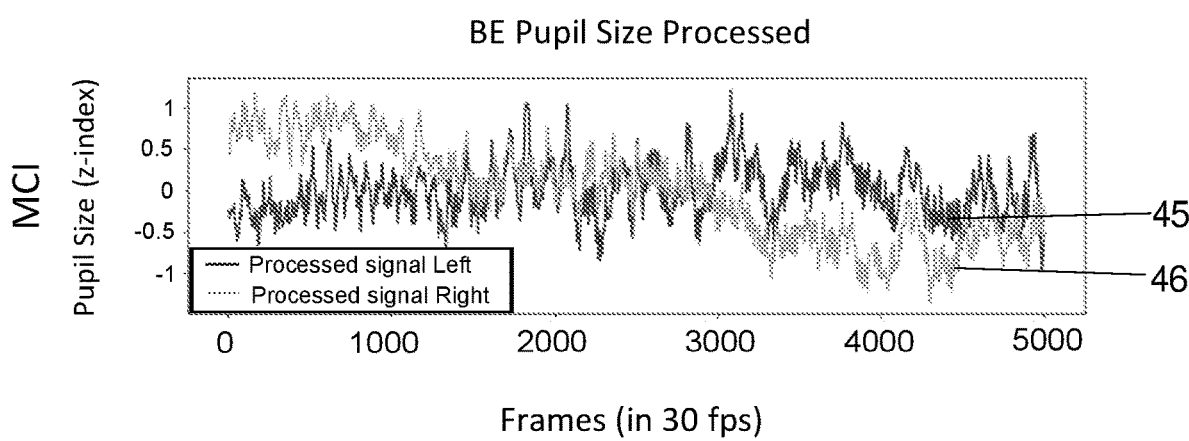
Figure 5:
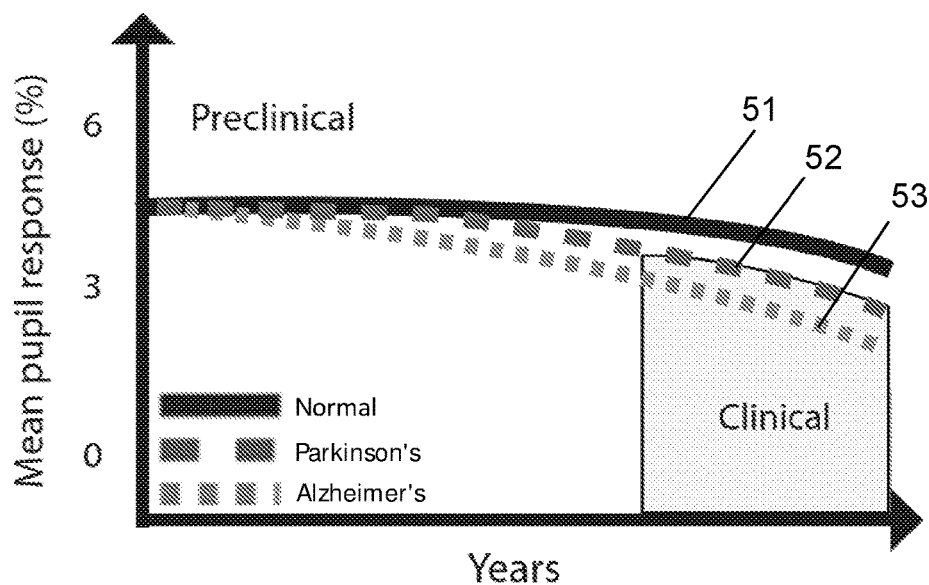
FIG. 5 is a schematic Illustration of mean pupil dilation metrics over the progress of years in healthy relative to neurodegenerative disorder (Alzheimer's and Parkinson's) aging populations according to an embodiment of the invention.

In an embodiment of the invention one of the eye-markers extracted from the mobile device is the pupil size of the eye. Pupil average size in humans is known to decrease with age. In AD patients in particular, pupil size is even smaller than in normal aging (apparently due to loss of LC neuronal mass), leading to reduced tonic NE levels. Reduced pupil response, which is more acute in AD, but exists also in PD patients indicates that over long periods of time the higher pupil fluctuation frequency bands (in the range of 0.2-1 Hz) should show reduced power relative to their past personal levels and likely also relative to past and existing power of tonic low frequency bands (0.01-0.1 Hz). Results of experiments made by the inventors are schematically presented in FIGS. 4a-ac, where it can be seen that reduced power in the high frequency bands is typical in the pupil-size time-course of PD patients, here specifically in the left eye (see line 44 relative to right eye in line 43). In contrast, the MCI patients typically show reduction and asynchrony in the lower frequency bands as can be seen when comparing lines 45 and 46, relative to the coherent pupil-size time-courses of a normal subject, as shown in lines 41 and 42. FIG. 5 illustrates the long term trend of the mean pupil dilation response to typical experimental events as expected during the progression of AD and PD, relative to the normal-healthy population. Line 51 shows the normal size of mean pupil response as function of time; line 52 shows the mean pupil response of PD patients and line 53 shows the expected mean pupil response of AD patients. The results were adapted and merged into a single representation from separate findings. These findings indicate that a smaller dilation effect is expected in cognitive decline relative to normal aging population. Further separation between different variants of neurodegeneration disease may be supported as well, as shown in the decoherency effect between pupils of both eyes in an MCI patient (shown in FIG. 4) that may evolve during the progression of the disease. Preclinical MCI (potentially leading to Alzheimer's) patients are expected to demonstrate larger variance or decline in the mean response, relative to preclinical Parkinson's patients due to known higher rate of neuronal tissue loss in the LC (leading to decreased NE emission). In the context of seamless background device operation, in which no specific task-responses exist, a frequency-amplitude analysis, separating out the canonical pupil responses to natural ongoing events substitutes the ordinary experimental settings. Additional abnormal aging effects found in pupil response that may be of relevance for the present invention include the following:

(a) older subjects (~50-70 years old) show an increase in latency and decreased velocity of constriction for specific wavelengths of light (i.e. to explicit colors) compared to younger subjects (~20-40 years old).

(b) Significantly larger pupil diameters, with anisocoria (unequal pupil sizes) after light adaptation (and in general), are known to exist in PD patients. In addition, longer light reflex latencies and constriction times were observed while contraction amplitudes were reduced. These results may suggest an LC, autonomic and possibly also cortical imbalance in PD patients.

Figure 6A:
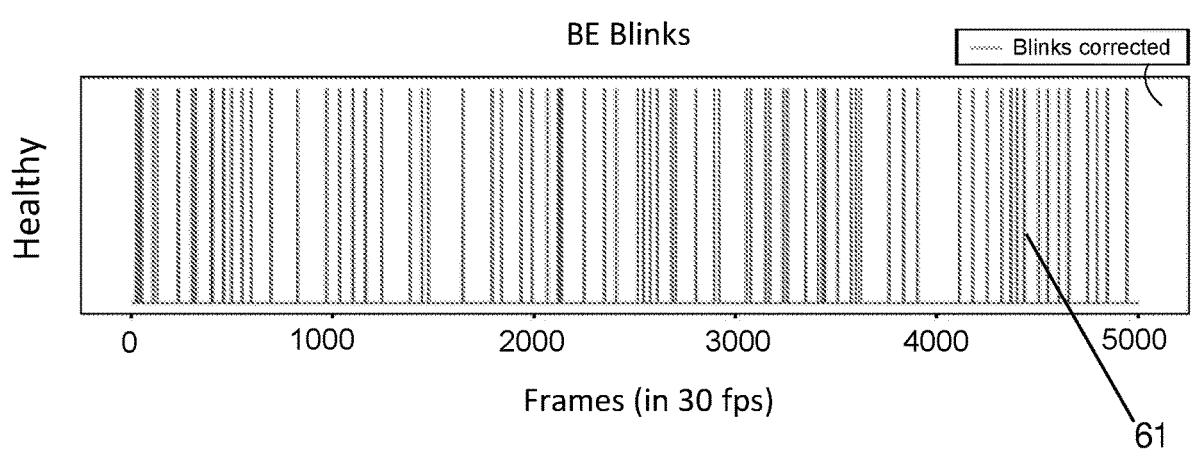
FIGS. 6a-6c schematically presents and compares spontaneous blink time-course results from normal, Parkinson's and MCI users of the technology according to an embodiment of the invention.
Figure 6B:
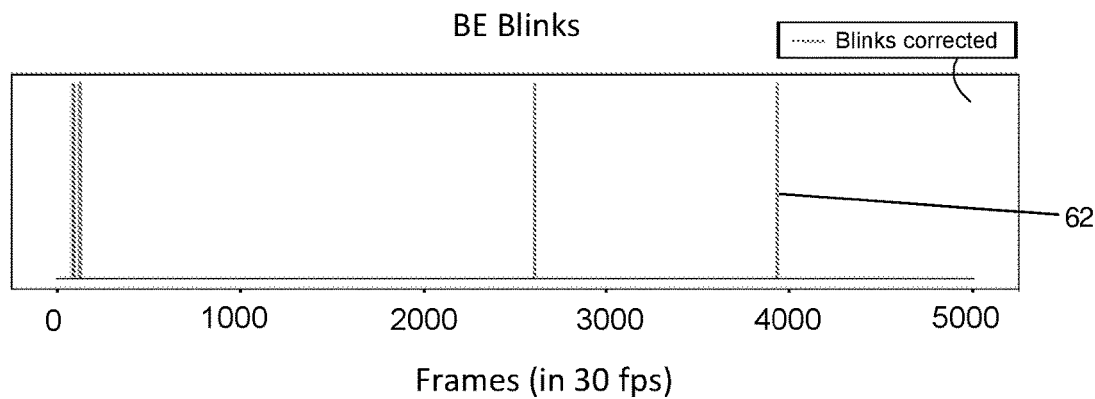
Figure 6C:
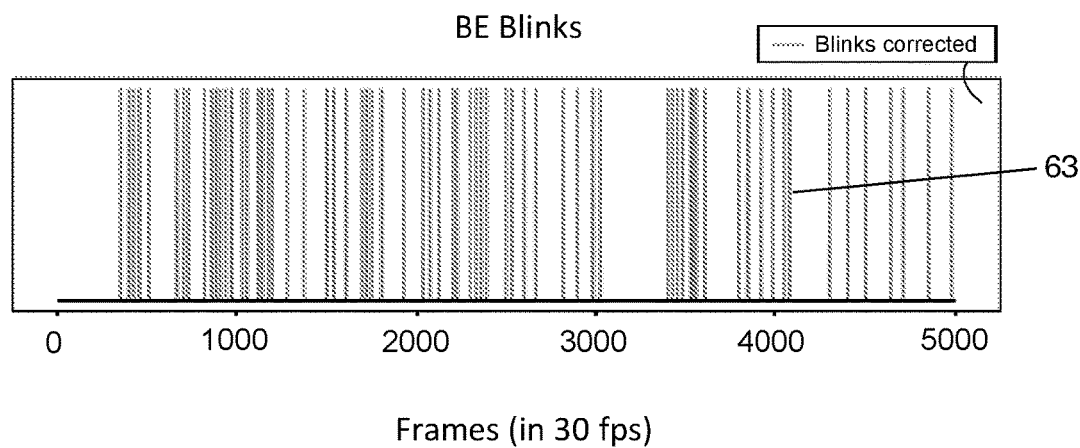

In another embodiment of the invention, a spontaneous blink rate (SBR) related eye-marker is extracted from the mobile device. Neurodegeneration is known to bare an effect on the SBR. The origin of this effect was found to lie in the dopaminergic system. Patients with PD exhibit a reduced frequency of spontaneous blinking (roughly 12-16 blinks/minute) relative to the normal rate (20-22 blinks/minute), leading to a staring appearance. In PD, the blink reflex may also not disappear on repeated tapping. In addition, blink duration is typically increased due to the loss of dopamine neurons. Interestingly and in contrast, the spontaneous blink rate of MCI and early AD patients shows an increase in the variability and in the maximal rate (to 26-28 blinks/minute) relative to the normal rate. Results of experiments made by the inventors, from typical clinical and healthy subjects, as shown in FIGS. 6a-6c, illustrate an exact match with these general observations about the spontaneous blink signals. Relative to the uniform blink rate of a normal subject (see line 61), the blink rate in PD falls steeply (in line 62) and is highly irregular or faster than normal in MCI (see line 63).

Figure 7:
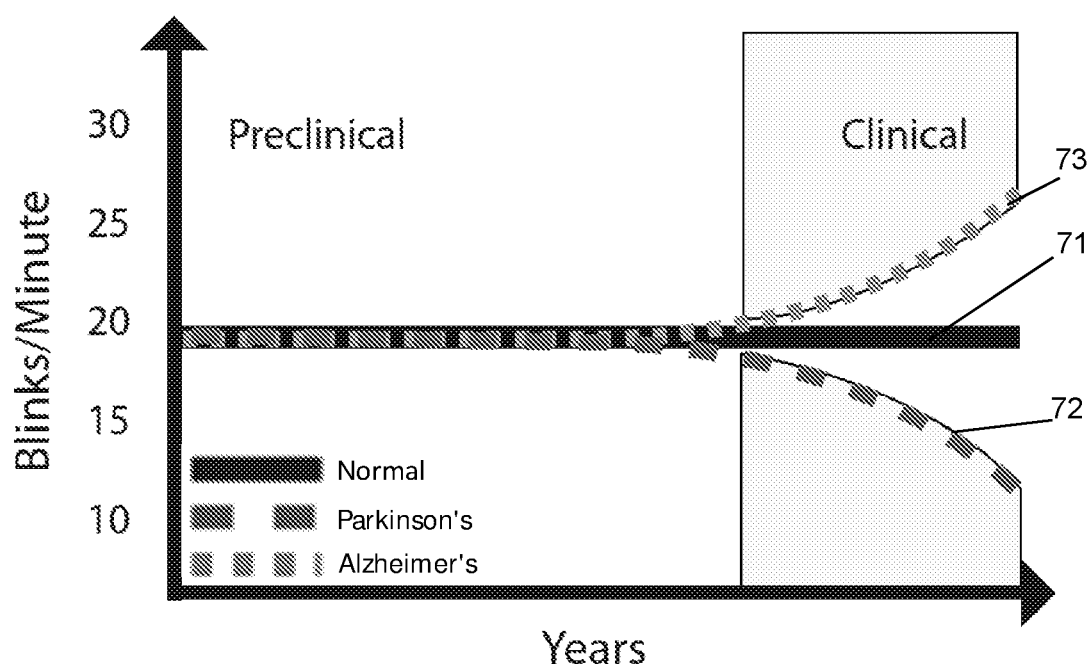
FIG. 7 is a schematic Illustration of the spontaneous rate of blinks (per minute) in normal aging and neurodegenerative disorder (Alzheimer's and Parkinson's) populations, over the progress of years according to an embodiment of the invention.

FIG. 7 schematically illustrates these SBR results over the course of longer periods of time, comparing and separating between AD represented by line 73, PD represented by line 72 and normal populations represented by line 71. The results demonstrate the converse effects expected in the clinical and normal populations.

Figure 8:
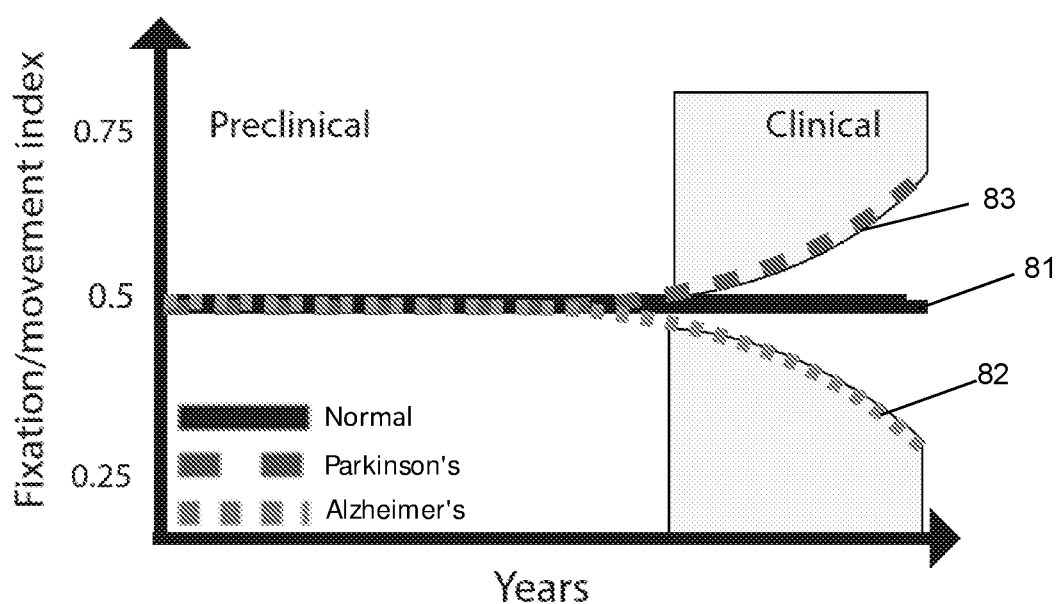
FIG. 8 is a schematic Illustration of the typical change in eye movements due to neurodegenerative diseases relative to the normal population patterns, over the progress of years according to an embodiment of the invention.

In another embodiment of the invention eye-movements are used as an eye-marker relevant for the detection of neurodegeneration. Even when eye movements appear normal during clinical examination of pre-symptomatic individuals, professional eye-tracking recordings can nonetheless reveal prolonged eye movements disorders. Such disorders were shown to become increasingly significant with decline severity. In AD, the fixations are longer and the saccade amplitudes are smaller. PD patients, suffer from difficulties in sustaining repetitive actions, leading to anomalous smooth pursuit movements. PD patients also exhibit a reduction in saccade velocity, implying longer movements (in scale of ~100 ms) between fixation periods. These eye movement trends can be captured with an index based on fixation over movement times, i.e. measuring the mean ongoing period of fixations and dividing them by mean period of movement. In AD patients, this index is expected to show an increase trend relative to normal population, where as in PD it is expected to decrease. FIG. 8 schematically illustrates gradual aging trends in eye-movement measures comparing and separating between AD, PD and normal populations using a fixation over movement time index. A normalized index of mean periods of fixation over eye movement, shown to be flat in aging normal population (line 81), indicates rise during MCI and in AD patients as shown by line 82, mainly due to prolonged fixation. In contrast, the index shows a decrease in PD patients as shown by line 83; here due to extension in the typical span of eye movements.

In another embodiment of the invention, additional eye-movement anomalies that may be in use by the method of the invention include: Abnormal optokinetic nystagmus, convergence and jerkiness in PD patients. Vertical eye movements are often more impaired than horizontal movements. Convergence can be associated with relatively large exophoria (outward deviation of the eye), and the result is often diplopia (double vision). As for AD patients, it has been recognized that they suffer difficulty with reading. This appears partly due to suboptimal eye movements, which have been suggested to be linked to memory function. Research also shows that AD patients present increased latency when initializing voluntary eye movements, and show decreased eye movement velocity. These fixation and movement errors reflect damage to their neural generators within the cortex and the brainstem.

When attaining to the transformation of various eye-marker data into machine learning features, the system of the invention uses a few novel methods besides the use of standard statistical variables. For each of the abovementioned markers, expectancy periodic priors are computed, such as mean and standard deviation over relevant periods (day, week and month). The inter-periodic delta calculation for each eye-marker (e.g. between weeks or months) is used as features as well. Sliding window analysis of variance over different periods of time is used to generate variables for comparison between normal and abnormal neurodegenerative patient populations. Another method implements frequency-based features, using Fourier transform (FFT) of eye-marker signals for purpose of comparing power of different frequency bands and wavelet analysis for computing the power in different frequency domains, or concentrating on certain frequency bands. Specifically, these concentrate on relevant low frequency bands, such as Delta (0.5-3 Hz), Theta (3-8 Hz) and infra-slow (<0.1 Hz), known to play vital role in brain activity and its neuromodulation. Lastly, metrics of criticality including, but not limited to Lyapunov characteristic exponents and fractal dimension analysis of eye-marker time-series, are implemented as part of feature construction. The underlying assumption here is that the dynamics of the cortical system being sampled, via its influence on eye-markers, reflects shifts between changing (inhibition-excitation balance related) attractor states. Cortical spontaneous activity was shown to exhibit near phase transition critical dynamics, the ripples of which are reflected in eye-markers that are sampled.

The features derived by the above described processes are selectively used within scope of a multiclass machine learning classification algorithm to model abnormal cognitive decline trends. Additional data captured simultaneously from other sensors of the device, e.g. accelerometer data, can serve as complementary features for the machine learning model. The outcome model is then used to predict the case by case cognitive health of participating users of the device of the present invention. As an output of the multiple-feature model, a diagnostic tool (using the output as a biomarker) for the differentiation between various neurodegenerative conditions of the described spectrum of diseases is achieved, facilitating an assessment of the severity and stage of the disease. The implications of a physiological biomarker providing an ability to separate between normal-healthy and abnormal cognitively declining populations is expected to have important consequences.

In an embodiment of the invention the eye-markers can be extracted also by a camera of Virtual Reality or Augmented Reality devices, or also by a camera of wearable devices such as Google glasses.

All the above description of preferred embodiments has been provided for the purpose of illustration only and is not intended to limit the invention in any way, except as per the appended claims.

The invention claimed is:

1. A method for the early detection of neurodegeneration, comprising the steps of:
   a) extracting samples of a plurality of eye-markers of a user from a video stream captured by a visible light camera;
   b) loading said samples of said plurality of eye-markers to a big data repository, analyzing and consolidating them into one biomarker for detecting multiple disorders by means of training a machine learning model; and
   c) determining the risk of said user to develop a neurodegenerative disease using said trained machine learning model as part of an early detection screening or diagnosis process.

2. The method according to claim 1, further comprising analyzing said samples of plurality of eye-markers, transforming some of said samples into derived features, to generate multiple features optimized for use within a machine learning model, using computational preprocessing methods for feature extraction.

3. The method according to claim 2, wherein computational methods are selected from one or more of: Fourier transform, wavelet analysis differentiating certain frequency bands, criticality metrics based on Lyapunov exponents and fractal dimension analysis.

4. The method according to claim 1, wherein one or more eye markers are extracted at a time.

5. The method according to claim 1, wherein the eye-markers extracted include the following: pupil size, eye movements, blinks and gaze.

6. The method according to claim 2, wherein the eye-markers are collected separately from each eye of the user as separate features of the machine learning model.

7. The method according to claim 6, wherein the derived features are based on features of each eye separately or on a function of the features of the two eyes.

8. The method according to claim 1, wherein the step of extracting samples is performed using one of the following: webcam, smartphone front or back camera, a camera of a Virtual Reality device, a camera of an Augmented Reality device, a camera of a wearable device or near IR-based eye-tracker.

9. The method according to claim 1, wherein the analysis of eye-markers, machine learning and consolidation to biomarker take place over the cloud or on a local computer.

10. The method according to claim 1, wherein additional machine learning features, besides the eye-markers, are collected from other device sensors during the eye tracking sessions.

11. The method according to claim 1, further comprising a user registration step, wherein a face recognition algorithm is used during user registration to differentiate the identity of said user from other occasional users of the device.

12. A system for the early detection of neurodegeneration, comprising:
   a) a camera of a mobile device or of Virtual Reality device or of an Augmented reality device for capturing video of one or both of the eyes of a user and extracting a plurality of eye marker samples;
   b) a big data repository for aggregating said plurality of eye-marker samples over time; and
   c) a machine learning module for analyzing said captured plurality of eye marker samples for consolidating said plurality of eye markers into a trained machine learning model reflecting a single biomarker; thereby, providing a prediction of an early stage diagnosis determining the risk of said user to develop neurodegenerative diseases.

13. The method according to claim 1, wherein the consolidating step comprises applying the following supervised machine learning schema:

$$Y_j^i = H_\theta(x_i^k) + \varepsilon_i$$

in which
   $Y_j^i$ denotes the consolidated biomarker and the ground truth per sample during the model training process as a vector of multiclass labels for j classes, wherein i is a sample index;
   $H_\theta$ is a model mapping between eye-marker features and the one consolidated biomarker;
   $\theta$ denotes a squashing function, $x_i^k$ denotes a features matrix consisting of k raw and derived eye-marker features, and $\varepsilon_i$ is an error per sample which is minimized during the training process.

14. The method according to claim 1, wherein the early detection screening or diagnosis process is performed on a subject that is not manifesting other clinical symptoms of neurodegeneration.

15. The method according to claim 1, wherein the selected eye markers include variations in pupil size measured over a course of time of two minutes or longer.

16. The method according to claim 1, wherein the selected eye markers are measured over a period of multiple days, and the step of analyzing and consolidating comprises analyzing a trend of gradual change over said period.

* * * * *